United States Patent [19]

Newman

[11] Patent Number: 4,881,939
[45] Date of Patent: Nov. 21, 1989

[54] IMPLANTABLE HELICAL CUFF

[75] Inventor: Arnold L. Newman, Kensington, Md.

[73] Assignee: The Johns Hopkins University, Baltimore, Md.

[21] Appl. No.: 702,570

[22] Filed: Feb. 19, 1985

[51] Int. Cl.⁴ .............................................. A61B 17/12
[52] U.S. Cl. ...................................... 600/31; 128/325; 128/DIG. 25
[58] Field of Search ....... 128/326, 325, 327, DIG. 25, 128/DIG. 20, 346, 303 A, 344; 600/29, 30, 31

[56] References Cited

U.S. PATENT DOCUMENTS

| | | | |
|---|---|---|---|
| 1,366,121 | 1/1921 | Dorsey | 128/327 |
| 3,409,014 | 11/1968 | Shannon | 128/326 |
| 3,454,010 | 7/1969 | Lilligren et al. | 128/327 |
| 3,538,917 | 11/1970 | Selker | 128/DIG. 25 X |
| 3,750,194 | 8/1973 | Summers | 128/DIG. 25 X |
| 3,993,076 | 11/1976 | Fogarty | 128/327 X |
| 4,016,883 | 4/1977 | Wright | 128/325 |
| 4,256,094 | 3/1981 | Kapp et al. | 128/325 X |
| 4,391,148 | 7/1983 | Sainz et al. | 128/663 X |
| 4,406,281 | 9/1983 | Hubbard et al. | 128/327 X |
| 4,428,365 | 1/1984 | Hakky | 128/1 R |
| 4,498,473 | 2/1985 | Gereg | 604/96 X |
| 4,556,050 | 12/1985 | Hodgson et al. | 128/DIG. 25 X |

Primary Examiner—Michael H. Thaler
Attorney, Agent, or Firm—Robert E. Archibald

[57] ABSTRACT

The invention concerns an implantable, inflatable helical cuff which is wrapped about a tubular body member such as a nerve cord, esophagus, colon, intestine, or blood vessel in a pressure transferring relationship. The cuff may be completely inflated to function as an occluder, or partially inflated to function as a pressure sensor or transducer in an appropriate system.

38 Claims, 4 Drawing Sheets

IMPLANTABLE HELICAL CUFF

BACKGROUND OF THE INVENTION

The invention concerns an inflatable, helical cuff which is implantable and functions as an occluder, sensor, or transducer when intimately engaged with a tubular body member (e.g., nerve cord, esophagus, colon, intestine or blood vessel).

The accurate measurement of blood pressure is necessary, in the treatment of volatile hypertension, the diagnosis of arteriosclerosis, and in the prevention of strokes, for example. The least complicated blood pressure measuring device is the common non-invasive cuff which is fastened about a patient's arm and inflated. However, very accurate blood pressure measurement is not possible since atmospheric pressure directly influences the cuff's operation. Jackson discloses in U.S. Pat. No. 4,160,448 a cannula for determining blood pressure, which is inserted into the blood stream through a needle, to locate a flaccid, relaxed wall directly in the blood stream. The relaxed wall allows direct transmission of the blood pressure to a neutral liquid in the cannula. The pressure of the cannula's liquid is transmitted out of the blood vessel to a remote pressure responsive indicator. Use of such an invasive device obviously increases the risk of damage to and infection of the blood vessel. U.S. Pat. No. 4,190,057 to Hill et al concerns a device for determining the patency of a blood vessel. A bulb of flexible material is arranged in pressure transferring relationship with a wall of a vein. A cuff is tied around the bulb and the vein to hold them in a confined relationship. Connected by a catheter to the bulb is a thick walled reservoir which is implanted just under the patient's skin. The wall of the reservoir is punctured by a hypodermic needle which is connected to a pressure indicator.

Accurate blood flow measuring devices are generally calibrated to a blood vessel having zero velocity blood flow. To accomplish zero velocity in a blood vessel, occluders of an appropriate diameter, such as produced in various sizes by In Vivo Metric Systems, are used to close off the blood vessel. Such occluders consist of an inwardly inflatable C-ring which is tied about a blood vessel and inflated until the blood vessel is fully constricted. Because blood flow through the occluded area is impossible, a zero velocity measurement is obtainable. Other members of the body, such as the esophagus, colon, intestine, and nerve cords are occluded during surgery or for research purposes. However, these members are most often sewn, clipped or tied to prevent flow through the member.

Helical structures have been used in esophageal and cardiovascular grafts, as taught by U.S. Pat. Nos. 3,479,670 to Medell and 4,300,244 to Bokros, respectively. The esophageal graft includes a cylindrical tube which is wrapped with two sections of monofilament to form a right-hand helix and a left-hand helix along the surface of the tube. The resultant structure is heated, causing the monofilaments to fuse as a support for the tube. The cardiovascular graft uses a spring to join segments of a severed blood vessel. The spring may be joined at each end to the blood vessel segments by suturing or may be fitted to a rigid fitting which is secured about the blood vessel segments.

SUMMARY AND OBJECTS OF THE INVENTION

The invention concerns an implantable, inflatable, helical cuff having a fluid filled lumen that follows the spiral of the cuff. The cuff may be inflated with a pump or diaphragm when connected in fluidic communication to the lumen, or a hypodermic needle which pierces the cuff to add or subtract fluid from the lumen. A retaining device secures the coils of the cuff to prevent unwinding upon inflation. The retaining device is embodied as: a suture tied to the cuff ends; an adhesive applied between adjacent coils; a slotted sleeve, integral wrap, or reverse wound helix placed over the coils; or a reinforcing spring or rigid outer wall that extend the length of the cuff, paralleling the lumen. When fully inflated, the cuff functions as an occluder for a blood vessel, esophagus, nerve cord, colon, or intestine or the like. If partially inflated, the cuff may be used as a sensor or transducer in an associated system. In a sensor role, the cuff is fluidly connected to a reference pressure reservoir which may comprise a subcutaneous bulb, a rigid structure maintained at a selected pressure, or a venous coil. Pressure signals generated by the cuff and the reference pressure reservoir are compared, the resultant information reflecting the pressure sensed within a body member, e.g., blood vessel. The resultant pressure is indicated on a display. To function as a transducer, the cuff is connected to a driver which causes the cuff to generate energy waves through a body member to an associated detector. The associated detector may comprise a second coil which is wrapped about a blood vessel for measuring the flow of blood within.

It is, therefore, an object of the invention to:
realize an implantable inflatable helical cuff;
provide a pressure cuff wherein one size fits a variety of tubular body members having different diameters;
achieve a pressure cuff which functions as a tubular member pressure sensor, occluder and transducer;
provide a coiled pressure cuff which inflates only toward the cuff's central axis;
furnish an inflatable helical cuff which maintains its helix in an inflated or deflated condition; and
provide a pressure cuff which, when deflated, is loose for simple engagement with a tubular body member and is tight about the member when inflated.

BRIEF DESCRIPTION OF THE DRAWINGS

FIG. 8b is a detail of the wrap shown in FIG. 8a.

DETAILED DESCRIPTION OF THE INVENTION

Figure 1:
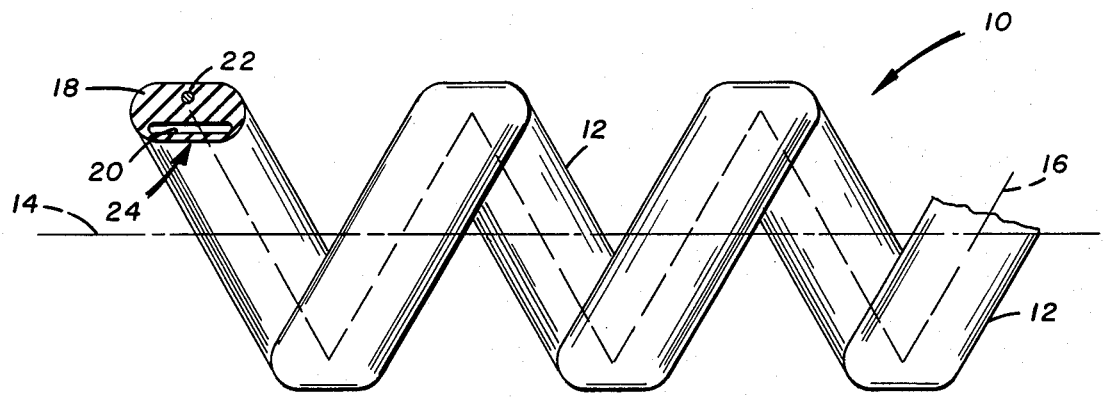
FIG. 1 shows a portion of the inflatable helical cuff.

FIG. 1 shows an apparatus comprising an implantable helical cuff at 10. The coils 12 of the cuff 10 turn about a central axis 14. The coils 12 also follow a spiral axis 16 about the central axis 14. The central and spiral axes 14, 16 are used as reference lines to which further details of the cuff 10 are relative. A cross-section of the cuff 10 is shown revealing an oval surface 18. An inflatable lumen 20 is shown in a deflated condition which, in its preferred embodiment, contains an isotonic liquid. A reinforcing spring 22 is also provided, giving the cuff 10 structural support. The lumen 20 and spring 22 follow the spiral axis 16 and are parallel. The cuff 10 is positioned within a patient's body such that central axis 14 substantially coincides with the longitudinal axis of an elongated body member, such as a blood vessel, esophagus, colon, intestine, or nerve cord. The coils 12 are then wrapped about the elongated member such that an inner wall 24 of the cuff 10 loosely engages the outer surface of the elongated member since the cuff 10 is deflated. Owing to the oval cross-section (see surface 18) of the cuff 10, the inner wall 24 is formed as a planar surface. The cuff cross-section may take many shapes, such as a circle, the inner wall 24 being substantially a linear surface.

Figure 2:
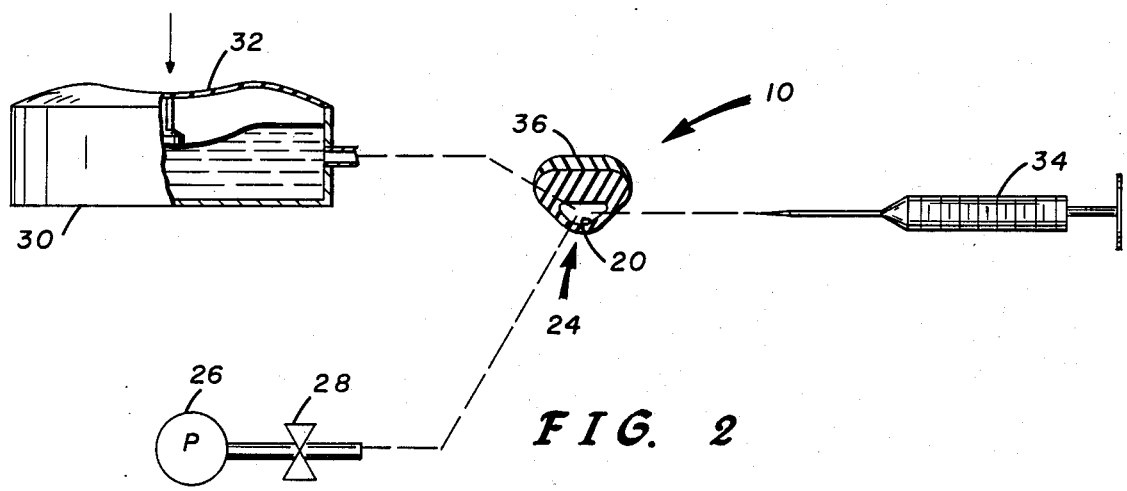
FIG. 2 shows a cross-section of the cuff as inflated by various devices.

FIG. 2 shows the cuff 10 as inflated. Inflation of the cuff is accomplished by the addition of fluid (e.g., air or isotonic liquid) to the lumen 20. A first fluid adding device is shown as a pump 26 which is in fluid connection with the lumen 20 and pumps fluid to and from the lumen 20. A valve 28 in line with the pump 26 may be provided to regulate flow of fluid to the lumen 20. The pump/valve filling device is generally known in the biomedical field, and is, therefore, not discussed in further detail. As an alternative, a diaphragm mechanism 30 may be fluidly connected to pump fluid to the lumen 20 when a button 32 is pushed. Additionally, a hypodermic needle 34 may be used to add or subtract fluid by piercing the inner wall 24 of the cuff 10. Instead of a reinforcing spring, the cuff 10 portrayed in FIG. 2 has a rigid outer wall 36 which maintains the coils 12 in their relative position. Without a reinforcing spring or rigid outer wall, inflation of the cuff 10 may cause the coils 12 to spread, rather than causing the lumen to extend inward. In response to a very high pressure, the cuff, without a structural reinforcing means, might unwind.

Figure 3:
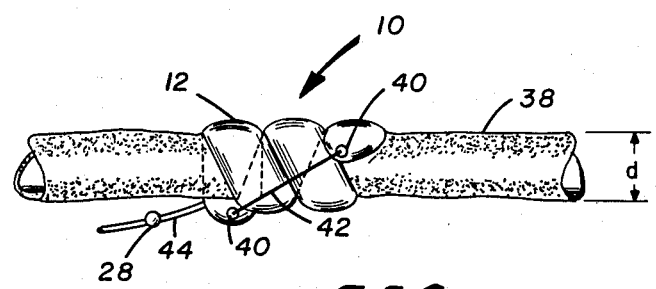
FIG. 3 shows the cuff tied about an artery of diameter d.

In FIG. 3 the cuff 10 is wrapped about an artery 38 of diameter d. In this embodiment, either end of the cuff 10 is provided with a hole 40, to which a suture 42 is tied. Upon inflation of the cuff 10, the suture 42 prevents the spreading or unwinding of the coils 12 so that the lumen (not visible) expands inwardly into a pressure transferring relationship with the artery 38. Tubing 44 fluidly connects the lumen 20 to the valve 28 and continues to the pump 26 of FIG. 2.

Figure 4:
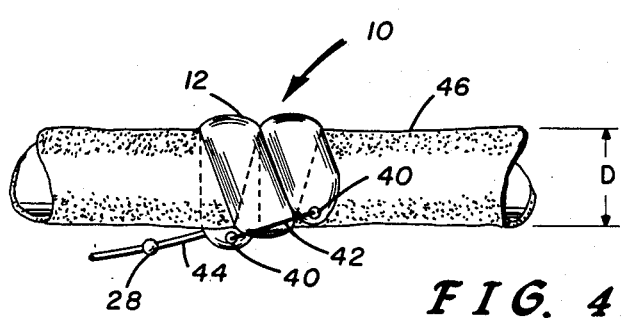
FIG. 4 shows the cuff of FIG. 3 as wrapped about an artery of diameter D.

FIG. 4 shows the cuff of FIG. 3 as wrapped about an artery 46 having diameter D. As is evident, fewer coils 12 wrap around the artery 46 than the artery 38 due to the larger diameter of artery 46. For engagement of either artery 38, 46, the cuff 10 is wound about the artery much like a telephone cord may be wound about a pencil. As is apparent, an important feature of this invention is the ability of a single cuff to engage arteries of various diameters.

Figure 5:
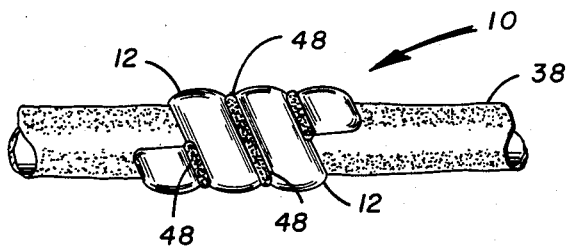
FIG. 5 shows the cuff retained about an artery by an adhesive.
Figure 6:
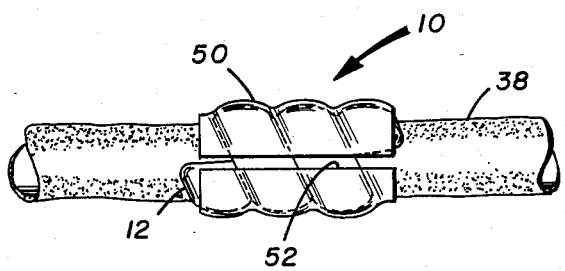
FIG. 6 shows a sleeve retaining the cuff about an artery.
Figure 7:
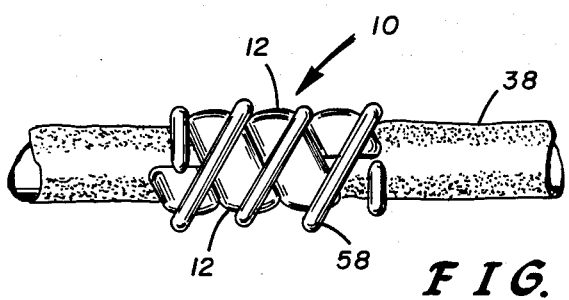
FIG. 7 shows a winding member which is reversed-wound about the cuff.
Figure 8B:
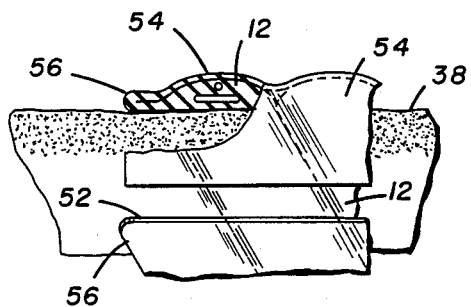
Figure 8A:
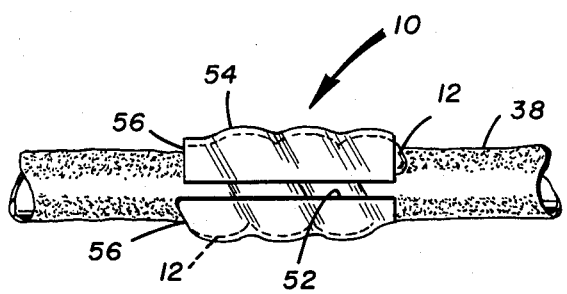
FIG. 8a shows an integral wrap retaining the cuff.

Various devices may be used to retain the coils 12 in their proper relationship about the artery 38. In FIG. 5, an adhesive 48, such as Dow-Corning's Medical Adhesive A, is used to adhere adjacent coils 12 of the cuff 10. In FIG. 6 a sleeve 50 is portrayed about the cuff 10. The sleeve 50 has a lengthwise slot 52 giving the sleeve 50 a C-cross-section. The lengthwise slot 52 is opened so that the sleeve 50 may be slipped over the cuff, the natural resiliency of the sleeve 50 causing the sleeve 50 to close about the cuff 10. FIG. 7 shows another means for retaining the cuff about the artery 38. Here a helical or winding member 58 is wound over the cuff 10, counter to the turns of coils 12. The embodiment of FIG. 8a reveals a wrap 54 which is integral at one end with the cuff 10. The details of the wrap 54 and its relationship to the coils 12 are apparent in FIG. 8b, which is an expanded, cut-away view of the upper left portion of the cuff 10 portrayed in FIG. 8a. Specifically, the wrap 54 is joined to the cuff 10 by a crease 56. Once the cuff 10 is placed about the artery 38, the wrap 54 is opened at slot 52 and folded back upon cuff 10 (see FIG. 8a).

Figure 9:
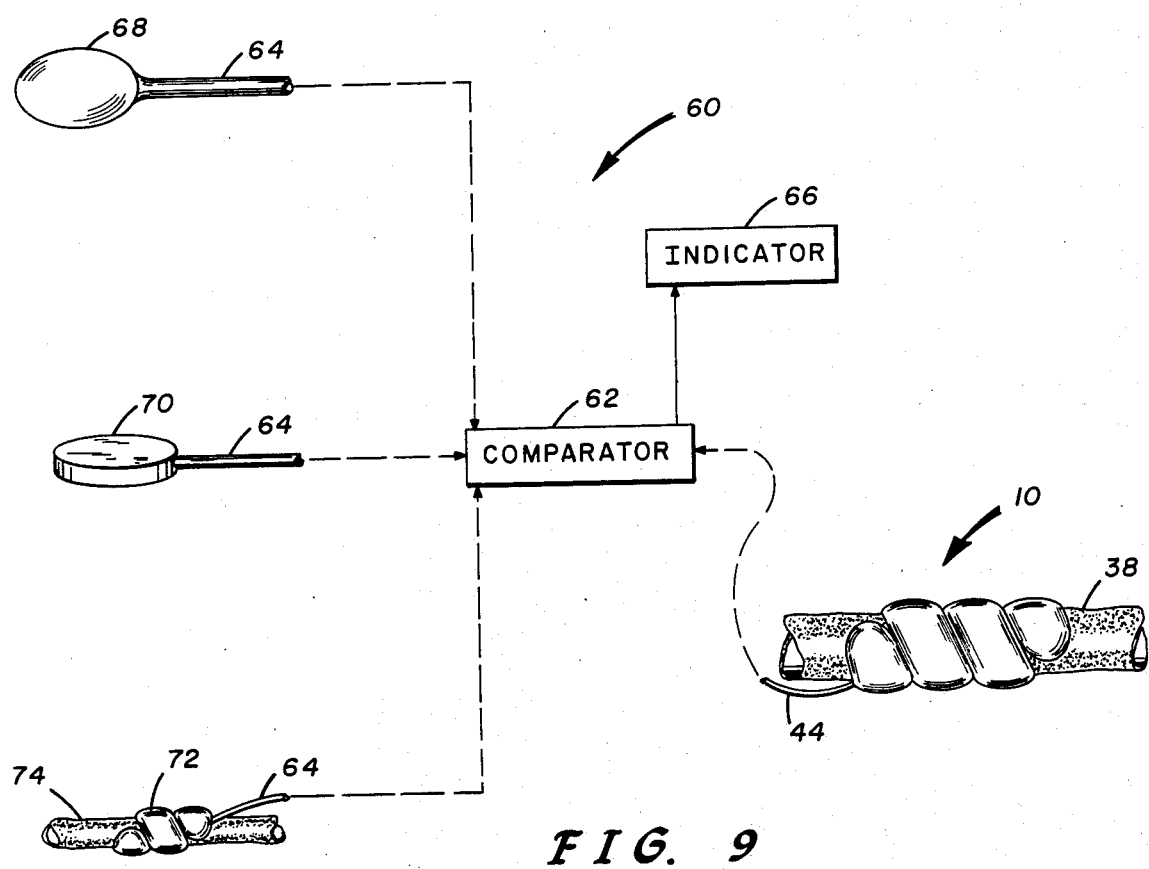
FIG. 9 shows the cuff in a sensor system with various reference pressure reservoirs.

FIG. 9 shows an apparatus including a sensor system at 60 which incorporates the inflatable helical cuff 10. The sensor system 60 includes a pressure reservoir for generating a reference pressure value. Three such reference pressure reservoirs are shown fluidly connected to a comparator 62 by means of tubing 64. The comparator 62 also receives a signal from the cuff 10 via tubing 44, the signal representing the pressure detected in artery 38. The comparator 62 derives the differences between the pressure sensed by the cuff 10 and the reference pressure reservoir to determine the actual pressure within the artery 38. The actual pressure is displayed on an indicator 66 (e.g., gage, digital readout). The comparison between the sensed pressure and reference pressure is made to compensate for pressure changes external to the system. In one instance, the reference pressure reservoir comprises a bulb 68 which is implanted in the vicinity of the cuff 10; however, the bulb 68 does not contact the artery. Any change in external pressure, due to an elevation change, for instance, will effect the pressure values sensed by the cuff 10. However, this change in pressure will similarly effect the bulb 68. The comparator 62, in turn, will generate a value which represents the pressure actually occurring in the blood vessel 38. In another embodiment, the reference pressure reservoir may comprise a sealed cannister or other rigid structure 70, wherein the fluid pressure is maintained at a constant level of one atmosphere, for instance. The cuff 10 generates a signal indicating pressures due to the ambient pressure and that within the artery 38, the cuff-generated signal being compared to the constant pressure within the rigid structure 70. In the preferred embodiment, the reference pressure reservoir comprises a venous helical cuff 72 of one or two coils, which is easily wrapped about a patient's vein 74. The venous cuff 72 is preferred because, not only will it respond to ambient pressures, the venous cuff 72 will compensate for muscular contraction of the blood vessels, or dilation of the vessels in response to an increased Adrenalin levels within the patient, for instance.

Figure 10:
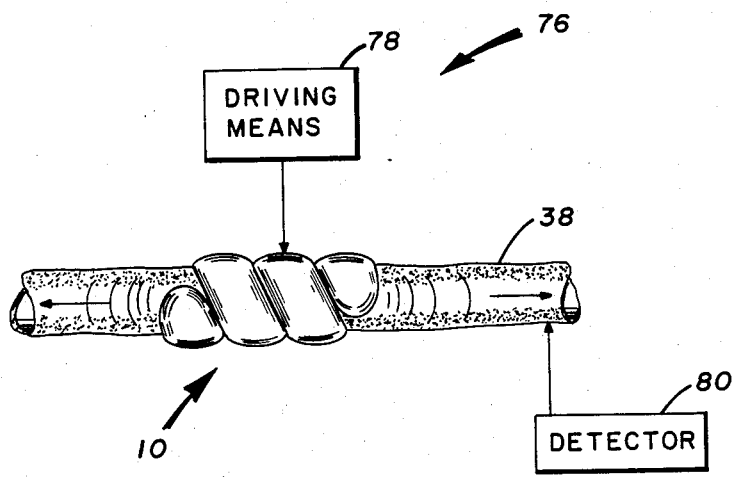
FIG. 10 shows the cuff in a transducer system.

FIG. 10 reveals an apparatus which includes the cuff 10 and a transducer system generally at 76. In this system, the cuff 10 is actuated by a driving means such as an ultrasonic piezoelectric transducer 78, the cuff 10 acting as a transducer generates waves along the artery 38, (or other tubular body member), these energy waves comprising sound waves or ultrasonic waves. Spaced along the artery 38 from the cuff 10 is a detector 80 which senses the waves propagated by the cuff 10. Alternatively, the detector may be incorporated in the transducer as a unit. The time delay or frequency shift in the waves generated from the cuff 10 to the detector 80 are indicative of blood flow in the artery 38. The detector 80 may comprise a second inflatable helical cuff acting as a sensor in a system as discussed with respect to FIG. 9.

Figure 11:
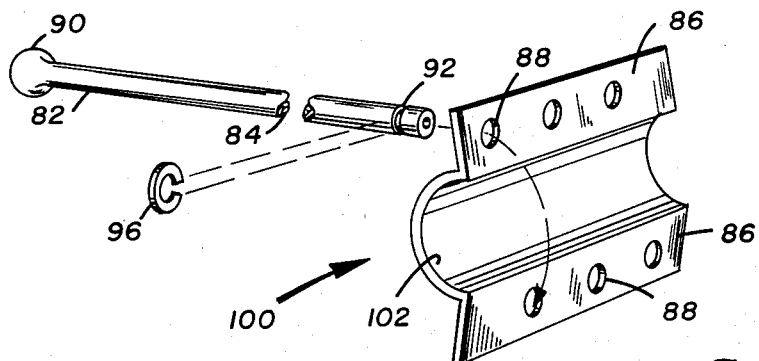
FIG. 11 shows another realization of an inflatable cuff which may be coiled.

FIG. 11 shows another realization of an inflatable cuff which may be coiled about an elongated body member. In this embodiment the cuff includes a tube 82 with a fluid-containing, concentric lumen 84. The tube 82 is threaded through a flanged member 100 which comprises two plates 86 having holes 88 which orient the tube 82 into coils along a spiral axis. A bead 90 is provided at one end of the tube 82 which prevents the tube 82 from slipping through the holes 88. At the distal end of the tube 82, an annular slot 92 is shown about which clip 94 is forced once the tube 82 is threaded through the plates 86 of the flange member 100.

Figure 12A:
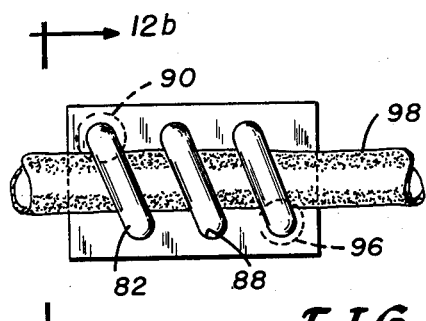
FIG. 12a shows a plate securing an inflatable tube in a helix about an artery.

FIG. 12a shows the tube 82 as threaded. Here, the tube 82 is intimately engaged with an artery 98, the tube 82 being coiled as guided through the flanged member 100.

Figure 12B:
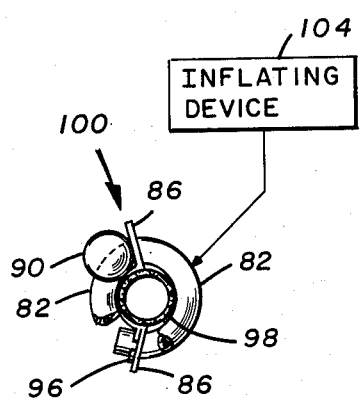
FIG. 12b is a side view of the FIG. 12a apparatus.

FIG. 12b shows an end view of the cuff as portrayed in FIG. 12a. It is evident that the bead 90 and clip 96 retain the tube 82 about the artery 98. A curved surface 102 is provided in the flanged member 100, providing a complementary surface for engaging the outer surface of the artery 98. As with prior embodiments, the tube 82 may be inflated into a proper pressure transferring relationship by means of an inflating device 104, which may comprise a hypodermic needle, pump or diaphragm, which adds fluid to or subtracts fluid from the lumen 84 (see FIG. 11).

Figure 13A:
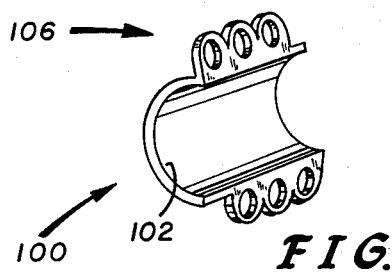
FIG. 13a, b and c portray three additional means for securing the tube of FIG. 12a to an artery.
Figure 13B:
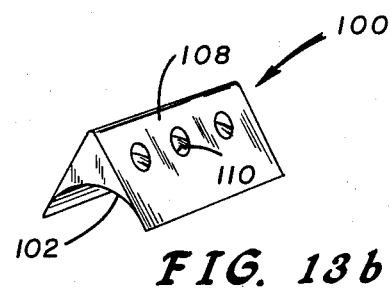
Figure 13C:
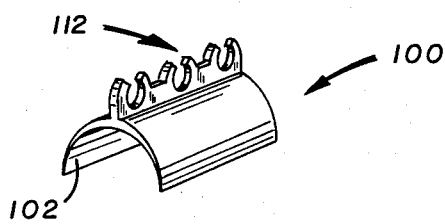

FIGS. 13a, b, c reveal additional embodiments of flanged members for orienting the tube 82 into coils about an artery or other elongated body member. In FIG. 13a a flanged member 100 with a curved surface 102, includes a series of rings 106, which orient tube 82 into coils about an artery in the manner of the flanged member 100 of FIGS. 11, 12a, and 12b. FIG. 13b shows a flanged member 100 having two faces which are angularly joined, and which are connected by holes 110. The tube 82 is threaded through one hole of one of the holes 110 about the artery and through an adjacent one of the holes 110. FIG. 13c shows another version of the flanged member 100; however, in this case, the flanged member comprises a series of clip rings 112 for securing the tube 82 in a helical fashion about an artery or other elongated body member.

What is claimed is:

1. An implantable inflatable cuff which intimately engages the exterior of an elongated body member, the implantable inflatable cuff comprising:
   a coil which follows a spiral axis and turns about a central axis, said coil having a cross sectional shape that remains constant throughout its length, an elastic inside wall facing said central axis, a lumen within said coil and eccentric to said spiral axis and a fluid contained within said lumen; and
   a retaining means which is removably positioned about and extends across a plurality of turns of said coil for maintaining said coil in said spiral axis.

2. An apparatus as in claim 1, the retaining means comprising a sleeve which is slipped over the cuff.

3. An apparatus as in claim 2, including a comparing means, and a reference pressure means which generates a reference pressure value to the comparing means, the cuff detecting pressure within the elongated member and generating a sensed pressure value to the comparing means which generates an actual pressure value dependent on the reference pressure value and the sensed pressure value.

4. An apparatus as in claim 2, including a driving means connected to the cuff, causing the cuff to transduce energy waves through the elongated member.

5. An apparatus as in claim 1, the retaining means comprising a wrap which is integral with one end of the cuff and is folded over the coil.

6. An apparatus as in claim 5, including a comparing means, and a reference pressure means-which generates a reference pressure value to the comparing means, the cuff detecting pressure within the elongated member and generating a sensed pressure value to the comparing means which generates an actual pressure value dependent on the reference pressure value and the sensed pressure value.

7. An apparatus as in claim 5, including a driving means connected to the cuff, causing the cuff to transduce energy waves through the elongated member.

8. An apparatus as in claim 1, the retaining means comprising a winding member which is wound about the cuff counter to the cuff coil.

9. An apparatus as in claim 8, including a comparing means, and a reference pressure means which generates a reference pressure value to the comparing means, the cuff detecting pressure within the elongated member and generating a sensed pressure value to the comparing means which generates an actual pressure value dependent on the reference pressure value and the sensed pressure value.

10. An apparatus as in claim 8, including a driving means connected to the cuff, causing the cuff to transduce energy waves through the elongated member.

11. An apparatus as in claim 1, including a comparing means, and a reference pressure means which generates a reference pressure value to the comparing ;means, the cuff detecting pressure within the elongated member and generating a sensed pressure value to the comparing means which generates an actual pressure value dependent on the reference pressure value and the sensed pressure value.

12. An apparatus as in claim 11, the reference pressure means comprising a pressure reservoir bulb implanted in the vicinity of the cuff.

13. An apparatus as in claim 11, the reference pressure means comprising a pressure reservoir having a rigid structure, the internal pressure of which is maintained at a predetermined value.

14. An apparatus as in claim 11, wherein the cuff is coiled about an artery, the reference pressure means comprising a venous helical cuff which is coiled about a vein.

15. An apparatus as in claim 11, including a fluid pump connected to pump fluid to and from the cuff such that the elastic inside wall expands and contracts.

16. An apparatus as in claim 15, including a valve connected between the cuff and the pump for maintaining fluid in and releasing fluid from the cuff.

17. An apparatus as in claim 11, including a needle which pierces the cuff to add and remove fluid.

18. An apparatus as in claim 11, including a diaphragm member connected to the cuff for forcing fluid to and from the cuff.

19. An apparatus as in claim 1, including a driving means connected to the cuff, causing the cuff to transduce energy waves through the elongated member.

20. An apparatus as in claim 19, wherein the cuff transduces sound waves.

21. An apparatus as in claim 19, wherein the cuff transduces ultrasonic waves.

22. An apparatus as in claim 19, including a fluid pump connected to pump fluid to and from the cuff such that the elastic inside wall expands and contracts.

23. An apparatus as in claim 19, including a needle which pierces the cuff to add and remove fluid.

24. An apparatus as in claim 19, including a diaphragm member connected to the cuff for forcing fluid to and from the cuff.

25. An apparatus as in claim 1, including a fluid pump connected to pump fluid to and from the cuff such that the elastic inside wall expands and contracts.

26. An apparatus as in claim 1, including a needle which pierces the cuff to add and remove fluid.

27. An apparatus as in claim 1, including a diaphragm member connected to the cuff for forcing fluid to and from the cuff.

28. An apparatus as in claim 1, wherein said retaining means comprises a guide element in which said coil is threaded to follow the spiral axis.

29. An apparatus as in claim 28, including a clipping means, the tube having a bead at one end and an annular slot at another end which is engaged by the clipping means to secure the tube to the guide element.

30. An apparatus as in claim 29, the guide element having a curved surface which contacts the exterior of the elongated body member, and a coil orienting means which retains the tube along the spiral axis.

31. An apparatus as in claim 30, the flanged member comprising a plate, and the coil orienting means comprising holes through which the tube is threaded.

32. An apparatus as in claim 30, the flanged member comprising a series of rings which are integral with the curved surface, and through which the tube is threaded.

33. An apparatus as in claim 30, the flanged member having two faces angularly joined, and a series of holes which connect the two faces, the tube being threaded through the series of holes.

34. An apparatus as in claim 30, the flanged member having a series of clip-rings by which the tube is helically secured about the elongated body member.

35. An apparatus as in claim 30, including a comparing means, and a reference pressure means which generates a reference pressure value to the comparing means, the cuff detecting pressure within the elongated member and generating a sensed pressure value to the comparing means which generates an actual pressure value dependent on the reference pressure value and the sensed pressure value.

36. An apparatus as in claim 35, including an inflating means which connects to the tube to add fluid to and subtract fluid from the lumen.

37. An apparatus as in claim 36, including a driving means connected to the cuff, causing the cuff to transduce energy waves through the elongated member.

38. An apparatus as in claim 30, including a driving means connected to the cuff, causing the cuff to transduce energy waves through the elongated member.

* * * * *